United States Patent [19]

Arlt et al.

[11] 4,104,377
[45] Aug. 1, 1978

[54] DISUBSTITUTED-O-(1-FLUORO-2-HALOGENOETHYL)-PHOSPHORIC(PHOSPHONIC) ACID ESTERS, AND METHOD OF COMBATING INSECTS

[75] Inventors: Dieter Arlt, Cologne; Wolfgang Behrenz, Overath-Steinenbrueck; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 696,147

[22] Filed: Jun. 14, 1976

[30] Foreign Application Priority Data

Jun. 28, 1975 [DE] Fed. Rep. of Germany ....... 2528996

[51] Int. Cl.² ............................ A01N 9/36; C07F 9/09; C07F 9/40
[52] U.S. Cl. ............................ 424/222; 260/961; 260/963; 260/955; 424/225
[58] Field of Search .................. 260/963, 961, 955; 424/222

[56] References Cited

U.S. PATENT DOCUMENTS

| | | | |
|---|---|---|---|
| 2,947,773 | 8/1960 | Allen | 260/963 X |
| 3,453,348 | 7/1969 | Demarcq et al. | 260/963 |
| 3,980,738 | 9/1976 | Arlt et al. | 260/963 X |

*Primary Examiner*—Anton H. Sutto
*Attorney, Agent, or Firm*—Burgess, Dinklage & Sprung

[57] ABSTRACT

Disubstituted-O-[1-fluoro-2-halogeno-ethyl]-phosphoric (phosphonic) acid esters of the formula

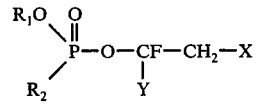

in which
$R_1$ is alkyl with 1 to 4 carbon atoms optionally substituted by fluorine, chlorine or bromine,
$R_2$ is alkyl or alkoxy each with 1 to 4 carbon atoms and optionally substituted by fluorine, chlorine or bromine, or phenyl optionally substituted by at least one of nitro and halogen,
X is chlorine or bromine, and
Y is hydrogen or fluorine,
which possess insecticidal, acaricidal and nematicidal properties.

12 Claims, No Drawings

DISUBSTITUTED-O-(1-FLUORO-2-HALOGENOETHYL)-PHOSPHORIC(PHOSPHONIC) ACID ESTERS, AND METHOD OF COMBATING INSECTS

The present invention relates to and has for its objects the provision of particular new disubstituted-O-[1-fluoro-2-halogeno-ethyl]-phosphoric(phosphonic) acid esters, which possess insecticidal, acaricidal or nematicidal properties, active compositions in the form of mixtures of such compounds with solid and liquid dispersible carrier vehicles, and methods for producing such compounds and for using such compounds in a new way especially for combating pests, e.g. insects, acarids, fungi and nematodes, with other and further objects becoming apparent from a study of the within specification and accompanying examples.

It is already known from U.S. Pat. Nos. 2,947,773 and 3,453,348 that chlorine-substituted or bromine-substituted alkylphosphoric (phosphonic) acid esters, for example O,O-diethyl-O-(1,2-dichloroethyl)-phosphoric acid ester (Compound A), are distinguished by insecticidal activity. However, these compounds suffer from the disadvantage of a very high toxicity to warm-blooded animals and a short duration of action. Furthermore, they are inactive as soil insecticides.

The present invention provides, as new compounds the 1-fluoro-2-halogeno-ethyl-phosphoric(phosphonic) acid esters of the general formula

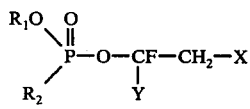  (I)

in which
R₁ is alkyl with 1 to 4 carbon atoms optionally substituted by fluorine, chlorine or bromine,
R₂ is alkyl or alkoxy each with 1 to 4 carbon atoms and optionally substituted by fluorine, chlorine or bromine, or phenyl optionally substituted by at least one of nitro and halogen,
X is chlorine or bromine, and
Y is hydrogen or fluorine.

These compounds have been found to possess outstanding insecticidal, including soil-insecticidal, acaricidal and nematicidal properties.

Preferably, R₁ is methyl, ethyl, 2-chloroethyl, 2-bromoethyl, n-propyl, isopropyl, 1-chloro-isopropyl, n-butyl, sec.-butyl, 2-chloro-1-fluoroethyl or 2-bromo-1-fluoro-ethyl and R₂ is methoxy, ethoxy, 2-chloroethoxy, 2-bromoethoxy, n-propoxy, isopropoxy, 1-chloroisopropoxy, n-butoxy, sec.-butoxy, 2-chloro-1-fluoroethoxy, 2-bromo-1-fluoroethoxy, methyl, ethyl, n-propyl, n-butyl or 2-chloroethyl.

The present invention also provides a process for the preparation of a 1-fluoro-2-halogenoethyl-phosphoric(-phosphonic) acid ester of the formula (I) in which (a) an alkyl ester of a phosphoric(phosphonic) acid of the general formula

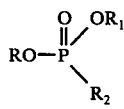  (II)

is reacted, in a one-step process, with chlorine or bromine and vinyl fluoride or vinylidene fluoride, of the formula

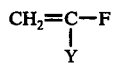  (III), or (b) a phosphoric(phosphonic) acid O-alkyl ester halide of the general formula

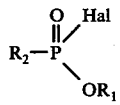  (IV)

is reacted simultaneously with chlorine or bromine and vinyl fluoride or vinylidene fluoride, and the 1-fluoro-2-halogenoethyl-phosphoric(phosphonic) acid ester halide obtained as an intermediate product, of the general formula

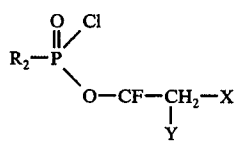  (V), is reacted, in a manner which is in itself known, either with an alcohol of the general formula

R₁OH  (VI)

in the presence of a tertiary organic base as an acid-binding agent, or with an epoxide of the general formula

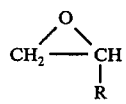  (VII), in which formulae (II) to (VII),
R₁, R₂, X and Y have the above-mentioned meanings,
R is C₁–C₄ alkyl, and
Hal is halogen.

If, for example, following process variant (a), O,O,O-trimethylphosphoric acid ester, chlorine and vinyl fluoride are used as starting materials, the course of the reaction can be represented by the following equation:

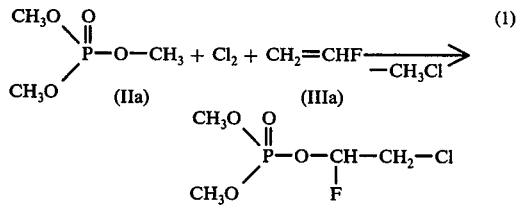  (1)

If, following process variant (b), O,O-dimethyl phosphoric acid ester chloride, vinyl fluoride, bromine and ethanol are reacted, the reaction takes place in accordance with the following equation:

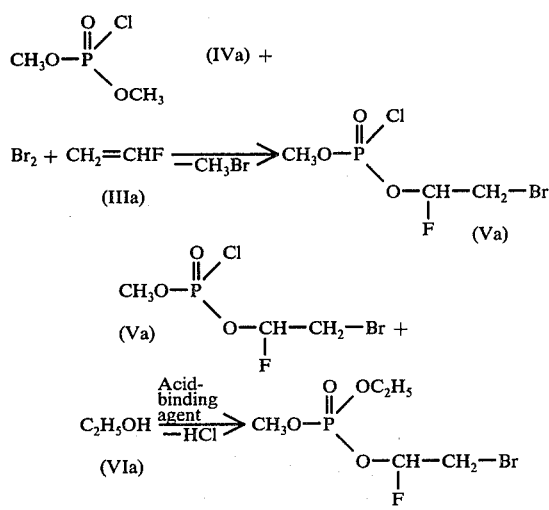

(18)

The following may be mentioned as examples of the fluorine-containing phosphoric(phosphonic) acid esters according to the invention: O,O-dimethyl-O-[1-fluoro-2-chloroethyl]-phosphoric acid ester, O,O-dimethyl-O-[1-fluoro-2-bromo-ethyl]-phosphoric acid ester, O,O-diethyl-O-[1-fluoro-2-chloro-ethyl]-phosphoric acid ester, O,O-diethyl-O-[1-fluoro-2-bromo-ethyl]-phosphoric acid ester, O,O-di-[2-chloroethyl]-O-[1-fluoro-2-chloroethyl]-phosphoric acid ester, O,O-di-n-propyl-O-[1-fluoro-2-chloro-ethyl]-phosphoric acid ester, O,O-di-i-propyl-O-[1-fluoro-2-chloro-ethyl]-phosphoric acid ester, O,O-di-n-butyl-[1-fluoro-2-chloro-ethyl]-phosphoric acid ester, O-methyl-O,O-di-[1-fluoro-2-chloroethyl]-phosphoric acid ester, O-methyl-O-[2-chloroethyl]-O-[1-fluoro-2-chloro-ethyl]-phosphoric acid ester, O-ethyl-O-[2-chloro-ethyl]-O-[1-fluoro-2-chloro-ethyl]-phosphoric acid ester, O-ethyl-O-[1,2-dichloro-ethyl]-O-[1-fluoro-2-chloroethyl]-phosphoric acid ester, methanephosphonic acid O-methyl-O-[1-fluoro-2-chloro-ethyl] ester, methanephosphonic acid O-ethyl-O-[1-fluoro-2-chloro-ethyl] ester, methanephosphonic acid O-[2-chloro-ethyl]-O-[1-fluoro-2-chloroethyl] ester, ethanephosphonic acid O-ethyl-O-[1-fluoro-2-chloroethyl] ester, ethanephosphonic acid O-ethyl-O-[1-fluoro-2-bromo-ethyl] ester, ethanephosphonic acid O-[2-chloro-ethyl]-O-[1-fluoro-2-chloro-ethyl] ester, ethanephosphonic acid O-i-propyl-O-[1-fluoro-2-chloro-ethyl] ester, 2-chloro-ethanephosphonic acid O-[2-chloro-ethyl]-O-[1-fluoro-2-chloro-ethyl] ester, 2-chloro-ethanephosphonic acid O-methyl-O-[1-fluoro-2-chloroethyl] ester, 2-chloroethanephosphonic acid O-ethyl-O-[1-fluoro-2-chloro-ethyl] ester, 2-chloroethanephosphonic acid O-methyl-O-[1-fluoro-2-bromo-ethyl] ester, propanephosphonic acid O-methyl-O-[1-fluoro-2-chloro-ethyl] ester, propanephosphonic acid O-methyl-O-[1-fluoro-2-bromo-ethyl] ester, propanephosphonic acid O-ethyl-O-[1-fluoro-2-chloro-ethyl] ester, propanephosphonic acid O-n-propyl-O-[1-fluoro-2-chloro-ethyl] ester, butanephosphonic acid O-methyl-O-[1-fluoro-2-chloro-ethyl] ester, benzenephosphonic acid O-methyl-O-[1-fluoro-2-chloroethyl] ester, 3-nitrobenzenephosphonic acid O-ethyl-O-[1-fluoro-2-chloroethyl] ester, O,O-dimethyl-O-[1,1-difluoro-2-chloroethyl]-phosphoric acid ester, O,O-dimethyl-O-[1,1-difluoro-2-bromoethyl]-phosphoric acid ester, O,O-diethyl-O-[1,1-difluoro-2-chloro-ethyl]-phosphoric acid ester, O,O-di-[2-chloro-ethyl]-O-[1,1-difluoro-2-chloro-ethyl]-phosphoric acid ester, methanephosphonic acid O-methyl-O-[1,1-difluoro-2-chloroethyl] ester, methanephosphonic acid O-ethyl-O-[1,1-difluoro-2-chloro-ethyl] ester and ethanephosphonic acid O-ethyl-O-[1,1-difluoro-2-chloro-ethyl] ester.

In general, the preparation of the 1-fluoro-2-halogenoethyl phosphoric(phosphonic) acid esters, according to process variant (a), is carried out by reacting stoichiometric amounts of the alkylphosphoric(phosphonic) acid ester (II), halogen and fluoroolefin (III); however, to achieve better yields, the use of an excess of the phosphorus-containing reagent can be of advantage. Furthermore, the use of an inert organic solvent or diluent is at times appropriate. As such it is preferred to use aliphatic or aromatic chlorinated hydrocarbons, such as chloroform, chlorobenzene, methylene chloride or dichloroethane.

In general, the reaction is carried out with external cooling, at temperatures of from −20° to +40°, and under normal pressure.

The reaction mixture can be worked up in accordance with customary methods, especially by fractional distillation.

The fluorine-containing phosphoric(phosphonic) acid esters of this invention are in most cases obtained in the form of colorless to pale yellow-colored water-insoluble oils which can be distilled under reduced pressure without undergoing decomposition. They can be characterised by their boiling point or boiling range.

As already mentioned, the present compounds are distinguished by very good insecticidal, acaricidal and nematicidal action; they also have a substantially lower toxicity to warm-blooded animals compared to known compounds of analogous structure and of the same type of action. They may therefore be used in plant protection and the protection of stored products, and in the hygiene field, for combating harmful sucking and biting insects, and also mites and nematodes.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly and moth caterpillars (Lepidoptera) such as the diamond-back moth (*Plutella maculipennis*) the gypsy moth (*Lymantria dispar*), the brown-tail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kühniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (Bruchidius = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzae philus surinamensis*), and also species living in the soil, for example wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as *Henschoutedenia flexivitta;* further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aëgypti*), the northern house mosquito (*Culex pipiens*) and the malaria mosquito (*Anopheles stephensi*).

With the mites (Acarina) there are classed, in particular, the spider mites (Tetranychidae) such as the two-spotted spider mite (*Tetranychus urticae*) and the European red mite (*Paratetranychus pilosus* = *Panonychus ulmi*), gall mites, for example the black currant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

When applied against pests harmful to health and pests of stored products, particularly flies and mosquitoes, the process products are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and-/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides and nematicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liter/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substances alone, e.g. about 20–100% by weight of the active compound.

When used against nematodes, the preprations are generally applied to an area of agriculture in amounts of 1 to 100 kg of active compound per hectare, and are then incorporated into the soil.

Furthermore, the present invention contemplates methods of selectively killing, combating or controlling pests, e.g. nematodes, insects and acarids, which comprises applying to at least one of correspondingly (a) such nematodes, (b) such insects, (c) such acarids and (d) the corresponding habitat thereof, i.e. the locus to be protected, e.g. to a growing crop, to an area where a crop is to be grown or to a domestic animal, a correspondingly combative or toxic amount, i.e. a nematicidally, insecticidally or acaricidally effective amount of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Drosophila test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all the flies were killed; 0% means that no flies were killed.

The active compounds, the concentrations of the active compounds, the evaluation times and the results can be seen from the following Table 1:

Table 1

| | (Drosophila Test) | |
|---|---|---|
| Active compound | Active compound concentration in % | Degree of destruction in % after 1 day |
| $Cl-CH_2-CH(Cl)-O-P(=O)(OC_2H_5)_2$ (known) (A) | 0.01<br>0.001<br>0.0001 | 100<br>100<br>0 |
| $(CH_3O)_2P(=O)-O-CF_2-CH_2-Cl$ (13) | 0.01<br>0.001<br>0.0001 | 100<br>100<br>100 |

EXAMPLE 2

Myzus test (contact action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following Table 2:

Table 2

| | (Insects which harm plants) Myzus test | |
|---|---|---|
| Active compound | Active compound concentration in % | Degree of destruction in % after 1 day |
| $(CH_3O)_2P(=O)-CH(OH)-CCl_3$ (known) (B) | 0.1<br>0.01 | 50<br>0 |
| $(CH_3O)_2P(=O)-O-CF_2-CH_2-Cl$ (13) | 0.1<br>0.01 | 100<br>100 |
| $CH_3-P(=O)(OCH_3)-O-CH(F)-CH_2-Cl$ (16) | 0.1<br>0.01 | 100<br>100 |

Table 2-continued (Insects which harm plants)
Myzus test

| Active compound | Active compound concentration in % | Degree of destruction in % after 1 day |
|---|---|---|
| $\underset{CH_3-P}{\overset{O}{\|}}\overset{OCH_3}{\diagup}$ $\diagdown O-CH-CH_2-Br$ $\quad\;\;\; \|$ $\quad\;\;\; F$ (7) | 0.1<br>0.01 | 100<br>98 |
| $\underset{C_2H_5-P}{\overset{O}{\|}}\overset{OC_2H_5}{\diagup}$ $\diagdown O-CH-CH_2-Br$ $\quad\;\;\; \|$ $\quad\;\;\; F$ (9) | 0.1<br>0.01 | 100<br>60 |
| $\underset{CH_3O-P}{\overset{O}{\|}}\overset{F}{\underset{\diagup}{\|}}\overset{O-CH-CH_2Cl}{}$ $\diagdown O-CH_2-CH_2Cl$ (10) | 0.1<br>0.01 | 100<br>85 |
| $\underset{CH_3-P}{\overset{O}{\|}}\overset{F}{\underset{\diagup}{\|}}\overset{O-CH-CH_2Cl}{}$ $\diagdown O-CH_2-CH_2Cl$ (14) | 0.1<br>0.01 | 100<br>100 |

EXAMPLE 3

Doralis test (systemic action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

Bean plants (*Vicia faba*) which had been heavily infested with the bean aphid (*Doralis fabae*) were watered with the preparation of the active compound so that this preparation penetrated into the soil without wetting the leaves of the bean plants. The active compound was taken up from the soil by the bean plants and thus passed to the infested leaves.

After the specified periods of time, the degree of destruction was determined as a percentage. 100% means that all the aphids were killed; 0% means that none of the aphids were killed.

The active compounds, the concentrations of the active compounds, the evaluation times and the results can be seen from the following Table 3:

Table 3

(Doralis Test/systemic action)

| Active compound | Active compound concentration in % | Degree of destruction in % after 4 days |
|---|---|---|
| $\underset{\text{(known) (B)}}{(CH_3O)_2\overset{O}{\overset{\|}{P}}-CH-CCl}$ $\qquad\qquad\quad \|$ $\qquad\qquad\quad OH$ | 0.1<br>0.01 | 100<br>0 |
| $(CH_3O)_2\overset{O}{\overset{\|}{P}}-O-CH-CH_2-Cl$ $\qquad\qquad\quad \|$ $\qquad\qquad\quad F$ (1) | 0.1<br>0.01 | 100<br>100 |
| $(CH_3O)_2\overset{O}{\overset{\|}{P}}-O-CH-CH_2-Br$ $\qquad\qquad\quad \|$ $\qquad\qquad\quad F$ (2) | 0.1<br>0.01 | 100<br>95 |
| $\underset{CH_3-P}{\overset{O}{\|}}\overset{O-CH_3}{\diagup}$ $\diagdown O-CH-CH_2-Cl$ $\quad\;\;\; \|$ $\quad\;\;\; F$ (6) | 0.1<br>0.01 | 100<br>100 |
| $\underset{CH_3-P}{\overset{O}{\|}}\overset{O-CH_3}{\diagup}$ $\diagdown O-CH-CH_2-Br$ $\quad\;\;\; \|$ $\quad\;\;\; F$ (7) | 0.1<br>0.01 | 100<br>100 |
| $\underset{C_2H_5-P}{\overset{O}{\|}}\overset{OC_2H_5}{\diagup}$ $\diagdown O-CH-CH_2-Cl$ $\quad\;\;\; \|$ $\quad\;\;\; F$ (8) | 0.1<br>0.01 | 100<br>100 |
| $\underset{C_2H_5-P}{\overset{O}{\|}}\overset{OC_2H_5}{\diagup}$ $\diagdown O-CH-CH_2-Br$ $\quad\;\;\; \|$ $\quad\;\;\; F$ (9) | 0.1<br>0.01 | 100<br>100 |
| $\underset{CH_3O-P}{\overset{O}{\|}}\overset{F}{\underset{\diagup}{\|}}\overset{O-CH-CH_2Cl}{}$ $\diagdown O-CH_2-CH_2Cl$ (10) | 0.1<br>0.01 | 100<br>100 |
| $\underset{CH_3-P}{\overset{O}{\|}}\overset{F}{\underset{\diagup}{\|}}\overset{O-CH-CH_2Cl}{}$ $\diagdown O-CH_2-CH_2Cl$ (14) | 0.1<br>0.01 | 100<br>100 |

EXAMPLE 4

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following Table 4:

Table 4
(Tetranychus Test/resistant)

| Active compound | Active compound concentration in % | Degree of destruction in % after 2 days |
|---|---|---|
| $Cl-CH_2-CH(Cl)-O-P(=O)(OC_2H_5)(OC_2H_5)$ (known) (A) | 0.1<br>0.01 | 60<br>0 |
| $(CH_3O)_2P(=O)-CH(OH)-CCl_3$ (known) (B) | 0.1 | 0 |
| $CH_3-P(=O)(OCH_3)-O-CH(F)-CH_2-Cl$ (6) | 0.1<br>0.01 | 99<br>55 |

EXAMPLE 5

Critical concentration test/soil insects
Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness is 100% if all test insects had been killed and is 0% if exactly as many test insects were still alive as in the case of the untreated control.

The active compounds, amounts used and results can be seen from the following Tables 5a and 5b:

Table 5a
Critical concentration test/soil insects
(*Phorbia antiqua* grubs in the soil)

| Active compound | Degree of destruction in % at an active compound concentration of 5 ppm |
|---|---|
| $Cl-CH_2-CH(Cl)-O-P(=O)(O-C_2H_5)(O-C_2H_5)$ (known) (A) | 0 |
| $(CH_3O)_2P(=O)-O-CH(F)-CH_2-Cl$ (1) | 100 |
| $(CH_3O)_2P(=O)-O-CH(F)-CH_2-Br$ (2) | 100 |
| $CH_3-P(=O)(O-CH_3)-O-CH(F)-CH_2Cl$ (6) | 100 |
| $Br-CH_2-CH(F)-O-P(=O)(O-C_2H_5)(O-C_2H_5)$ (4) | 100 |
| $Cl-CH_2-CH(F)-O-P(=O)(O-C_2H_5)(O-C_2H_5)$ (3) | 100 |
| $CH_3-P(=O)(OCH_3)-O-CH(F)-CH_2Br$ (7) | 100 |
| $C_2H_5-P(=O)(O-C_2H_5)-O-CH(F)-CH_2Cl$ (8) | 100 |
| $C_2H_5-P(=O)(O-CH(F)-CH_2Cl)-O-CH_2-CH_2-Cl$ (15) | 100 |
| $C_2H_5-P(=O)(O-CH(F)-CH_2Cl)-OCH_3$ (16) | 100 |

Table 5b

Critical concentration test/soil insects
*(Phorbia antiqua grubs in the soil)*

| Active compound | Degree of destruction in % at an active compound concentration of 20 ppm |
|---|---|
| $Cl-CH_2-CH(Cl)-O-P(=O)(O-C_2H_5)(O-C_2H_5)$ (known) (A) | 0 |
| $CH_3-O-P(=O)(O-CH(F)-CH_2Cl)(O-CH_2-CH_2Cl)$ (10) | 100 |
| $CH_3-P(=O)(O-CH(F)-CH_2Cl)(O-CH_2-CH_2Cl)$ (14) | 100 |
| $C_2H_5-P(=O)(O-CH(F)-CH_2Cl)(O-CH(CH_3)-CH_2Cl)$ (17) | 100 |

EXAMPLE 6

Critical concentration test/soil insects
Test insect: Tenebrio molitor larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness is 100% if all test insects had been killed and is 0% if exactly as many test insects were still alive as in the case of the untreated control.

The active compounds, amounts used and results can be seen from the following Tables 6a and 6b:

Table 6a

Critical concentration test/soil insects
*(Tenebrio molitor larvae in the soil)*

| Active compound | Degree of destruction in % at an active compound concentration of 10 ppm |
|---|---|
| $Cl-CH_2-CH(Cl)-O-P(=O)(O-C_2H_5)(O-C_2H_5)$ (known) (A) | 0 |
| $(CH_3O)_2P(=O)-O-CH(F)-CH_2-Cl$ (1) | 100 |
| $(CH_3O)_2P(=O)-O-CH(F)-CH_2-Br$ (2) | 100 |
| $CH_3-P(=O)(O-CH_3)(O-CH(F)-CH_2Cl)$ (6) | 100 |
| $Br-CH_2-CH(F)-O-P(=O)(O-C_2H_5)(O-C_2H_5)$ (4) | 100 |
| $Cl-CH_2-CH(F)-O-P(=O)(O-C_2H_5)(O-C_2H_5)$ (3) | 100 |
| $CH_3-P(=O)(OCH_3)(O-CH(F)-CH_2Br)$ (7) | 100 |
| $C_2H_5-P(=O)(O-C_2H_5)(O-CH(F)-CH_2Cl)$ (8) | 100 |
| $C_2H_5-P(=O)(O-C_2H_5)(O-CH(F)-CH_2Br)$ (9) | 100 |
| $CH_3-O-P(=O)(O-CH(F)-CH_2Cl)(O-CH_2-CH_2Cl)$ (10) | 100 |
| $CH_3-P(=O)(O-CH(F)-CH_2Cl)(O-CH_2-CH_2Cl)$ (14) | 100 |

Table 6a-continued

Critical concentration test/soil insects
(*Tenebrio molitor* larvae in the soil)

| Active compound | Degree of destruction in % at an active compound concentration of 10 ppm |
|---|---|
| $C_2H_5-\overset{O}{\underset{\|}{P}}\diagup\begin{array}{l}O-CH-CH_2Cl\\ \|\\ F\end{array}$ <br> $\diagdown\begin{array}{l}O-CH-CH_3\\ \|\\ CH_2Cl\end{array}$ (17) | 100 | there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from the following Table 7:

Table 7

($LT_{100}$ Test for *Diptera/Muscua domestica*)

| Active compound | | Active compound concentration in the solution, in % | $LT_{100}$ in minutes (') or hours (hrs) |
|---|---|---|---|
| $(CH_3O)_2\overset{O}{\underset{\|}{P}}-CH-CCl_3$ <br> $\qquad\quad\|$ <br> $\qquad\quad OH$ <br> (known) | (B) | 0.2 <br> 0.02 <br> 0.002 | 20' <br> 40' <br> 3 hrs = 0% |
| $(CH_3O)_2\overset{O}{\underset{\|}{P}}-O-CF_2-CH_2Cl$ | (13) | 0.2 <br> 0.02 <br> 0.002 | 5' <br> 10' <br> 30' |
| $CH_3-\overset{O}{\underset{\|}{P}}\diagup\begin{array}{l}O-CH_3\\ \\ O-CH-CH_2-Cl\\ \|\\ F\end{array}$ | (6) | 0.2 <br> 0.02 <br> 0.002 | 15' <br> 40' <br> 135' |
| $CH_3-\overset{O}{\underset{\|}{P}}\diagup\begin{array}{l}O-CH_3\\ \\ O-CH-CH_2-Br\\ \|\\ F\end{array}$ | (7) | 0.02 <br> 0.02 <br> 0.002 | 5' <br> 30' <br> 125' |

TABLE 6b

Critical concentration test/soil insects
(*Tenebrio molitor* larvae in the soil)

| Active compound | Degree of destruction in % at an active compound concentration of 20 ppm |
|---|---|
| $C_2H_4-\overset{O}{\underset{\|}{P}}\diagup\begin{array}{l}O-CH-CH_2Cl\\ \|\\ F\end{array}$ <br> $\diagdown O-CH_2-CH_2Cl$ (15) | 100 |

EXAMPLE 7

$LT_{100}$ test for Diptera
Test insects: *Musca domestica*
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish

EXAMPLE 8

$LT_{100}$ test for Diptera
Test insects: *Aedes aegypti*
Solvent: Acetone 2 parts by weight of active compound were dissolved in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. After 25 test insects were then placed in the Petri dish and it was covered with a glass lid.

The conditions of the test insects was continuously observed. The time which was necessary for 100% destruction was determined.

The test insects, the active compounds, the concentrations of the active compounds and the times at which there was 100% destruction can be seen from the following Table 8:

Table 8

(LT$_{100}$ Test for *Diptera/Aedes aegypti*)

| Active compound | Active compound concentration in the solution, in % | LT$_{100}$ in minutes (') or hours (hrs) |
|---|---|---|
| (CH$_3$O)$_2$—P(=O)—CH(OH)—CCl$_3$ (known) (B) | 0.2<br>0.02<br>0.002 | 60'<br>90'<br>3 hrs = 0% |
| (CH$_3$O)$_2$—P(=O)—OCH(F)—CH$_2$Cl (1) | 0.2<br>0.02<br>0.002 | 60'<br>120'<br>180' |
| Cl—CH$_2$—CH(F)—O—P(=O)(O—C$_2$H$_5$)$_2$ (3) | 0.2<br>0.02<br>0.002 | 60'<br>60'<br>3 hrs = 90% |
| (CH$_3$O)$_2$P(=O)—OCF$_2$—CH$_2$Cl (13) | 0.2<br>0.02<br>0.002<br>0.0002<br>0.00002 | 60'<br>60'<br>60'<br>60'<br>120' |
| CH$_3$—P(=O)(O—CH$_3$)(O—CH(F)—CH$_2$—Cl) (6) | 0.2<br>0.02<br>0.002 | 60'<br>60'<br>120' |
| C$_2$H$_5$—P(=O)(OC$_2$H$_5$)(O—CH(F)—CH$_2$—Cl) (8) | 0.2<br>0.02<br>0.002 | 60'<br>60'<br>180' |
| CH$_3$—P(=O)(O—CH$_3$)(O—CH(F)—CH$_2$—Br) (7) | 0.2<br>0.02<br>0.002 | 60'<br>60'<br>180' |
| C$_2$H$_5$—P(=O)(OC$_2$H$_5$)(O—CH(F)—CH$_2$—Br) (9) | 0.2<br>0.02<br>0.002 | 60'<br>60'<br>180' |
| CH$_3$O—P(=O)(OCH(F)—CH$_2$Cl)(OCH(F)—CH$_2$Cl) (5) | 0.2<br>0.02<br>0.002 | 60'<br>60'<br>180' |

EXAMPLE 9

Critical concentration test/root-systemic action
Test insect: *Phaedon cochleariae* larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (= mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all the test insects had been killed and 0% when just as many test insects were still alive as in the case of the untreated control.

The active compounds, the amounts used and the results can be seen from the following Tables 9a and 9b:

Table 9a

Root-systemic action
(*Phaedon cochleariae* larvae)

| Active compound | Degree of destruction in % at an active compound concentration of 10 ppm |
|---|---|
| Cl—CH$_2$—CH(Cl)—O—P(=O)(O—C$_2$H$_5$)$_2$ (known) (A) | 0 |
| CH$_3$—O—P(=O)(O—CH(F)—CH$_2$Cl)(O—CH$_2$—CH$_2$Cl) (10) | 100 |
| CH$_3$—P(=O)(O—CH(F)—CH$_2$Cl)(O—CH$_2$—CH$_2$Cl) (14) | 100 |
| C$_2$H$_5$—P(=O)(O—CH(F)—CH$_2$Cl)(O—CH(CH$_3$)—CH$_2$Cl) (17) | 100 |

Table 9b

Root-systemic action
(*Phaedon cochleariae* larvae)

| Active compound | Degree of destruction in % at an active compound concentration of 5 ppm |
|---|---|
| C$_2$H$_5$—P(=O)(O—CH(F)—CH$_2$Cl)(O—CH$_2$—CH$_2$Cl) (15) | 100 |

Table 9b-continued

Root-systemic action
(*Phaedon cochleariae* larvae)

| Active compound | Degree of destruction in % at an active compound concentration of 5 ppm |
|---|---|
| $C_2H_5-\overset{\overset{O}{\|}}{P}\underset{OCH_3}{\overset{O-\overset{\overset{F}{\|}}{CH}-CH_2Cl}{\diagup}}$ (16) | 100 |

EXAMPLE 10

Critical concentration test/root-systemic action
Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (= mg/1), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It is 100% when all the test insects had been killed and 0% when just as many test insects were still alive as in the case of the untreated control.

The active compounds, the amounts used and the results can be seen from the following Tables 10*a* and 10*b*:

Table 10a

Root-systemic action (*Myzus persicae*)

| Active compound | Degree of destruction in % at an active compound concentration of 5 ppm |
|---|---|
| $Cl-CH_2-\underset{Cl}{\overset{\|}{CH}}-O-\overset{\overset{O}{\|}}{P}\underset{O-C_2H_5}{\overset{O-C_2H_5}{\diagup}}$ (known) (A) | 0 |
| $CH_3-O-\overset{\overset{O}{\|}}{P}\underset{O-CH_2-CH_2Cl}{\overset{O-\overset{\overset{F}{\|}}{CH}-CH_2Cl}{\diagup}}$ (10) | 100 |

Table 10a-continued

Root-systemic action (*Myzus persicae*)

| Active compound | Degree of destruction in % at an active compound concentration of 5 ppm |
|---|---|
| $CH_3-\overset{\overset{O}{\|}}{P}\underset{O-CH_2-CH_2Cl}{\overset{O-\overset{\overset{F}{\|}}{CH}-CH_2Cl}{\diagup}}$ (14) | 100 |
| $C_2H_5-\overset{\overset{O}{\|}}{P}\underset{O-CH_2-CH_2Cl}{\overset{O-\overset{\overset{F}{\|}}{CH}-CH_2Cl}{\diagup}}$ (15) | 100 |
| $C_2H_5-\overset{\overset{O}{\|}}{P}\underset{OCH_3}{\overset{O-\overset{\overset{F}{\|}}{CH}-CH_2Cl}{\diagup}}$ (16) | 100 |

Table 10b

Root-systemic action (*Myzus persicae*)

| Active compound | Degree of destruction in % at an active compound concentration 10 ppm |
|---|---|
| $C_2H_5-\overset{\overset{O}{\|}}{P}\underset{O-\underset{CH_2Cl}{\overset{\|}{CH}}-CH_3}{\overset{O-\overset{\overset{F}{\|}}{CH}-CH_2Cl}{\diagup}}$ (17) | 100 |

EXAMPLE 11

Critical concentration test/nematodes
Test nematode: *Meloidogyne incognita*
Solvent: parts by weight
Emulsifier: parts by weight To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm, was decisive. The soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage: The degree of effectiveness was 100% when infestation was completely avoided; it was 0% when the infestation was exactly the same as in the case of the control plants in untreated soil which had been infested in the same manner.

The active compound, the amounts applied and the results can be seen from the following Table 11:

Table 11

Critical concentration test/nematodes
(*Meloidogyne incognita*)

| Active compound | Degree of destruction in % at an active compound concentration 20 ppm |
|---|---|
| Cl—CH$_2$—CH(Cl)—O—P(=O)(O—C$_2$H$_5$)(O—C$_2$H$_5$) (known) (A) | 0 |
| (structure 8) C$_2$H$_5$—P(=O)(O—C$_2$H$_5$)(O—CH(F)—CH$_2$Cl) (8) | 100 |
| (structure 16) C$_2$H$_5$—P(=O)(OCH$_3$)(O—CH(F)—CH$_2$Cl) (16) | 100 |

The process of the present invention is illustrated by the following Preparative Examples:

EXAMPLE 12

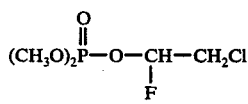
$$(CH_3O)_2\overset{O}{\underset{\|}{P}}-O-\underset{F}{\overset{|}{C}H}-CH_2Cl \quad (1)$$

35 g of chlorine and 70 g of vinyl fluoride were passed simultaneously into 250 g of O,O,O-trimethyl-phosphoric acid ester at −20° C while stirring and applying external cooling. After completion of the reaction, the methyl chloride formed and any dissolved vinyl fluoride were removed by warming the mixture to 50° C and the batch was subjected to fractional distillation. 99 g (97% of theory) of O,O-dimethyl-O-[1-fluoro-2-chloroethyl]-phosphoric acid ester of boiling range 76° to 77° C/0.4 mm Hg were obtained.

EXAMPLE 13

70 g of vinyl fluoride were passed into 212 g of O,O-dimethyl-phosphoric acid ester chloride at about 0° C, while stirring and applying external cooling, and at the same time 117 g of bromine were added dropwise. The reaction mixture was then degassed and subsequently subjected to fractional distillation. 120 g (65% of theory) of O-methyl-O-[1-fluoro-2-bromo-ethyl]-phosphoric acid ester monochloride of the formula Cl—PO-(OCH$_3$) (OCHF—CH$_2$Br) and of boiling range 80° to 83° C/0.2 mm Hg were obtained alongside 14 g of O,O-di-[1-fluoro-2-bromoethyl]-phosphoric acid ester monochloride of the formula Cl—PO(OCHF—CH$_2$Br)$_2$ and of the boiling range 100° to 105° C/0.15 mm Hg. These ester chlorides could be reacted with alcohols or epoxides in a manner which is in itself known, for example in accordance with U.S. Pat. No. 2,610,978 or Houben-Weyl: "Methoden der organischen Chemie" ("Methods of Organic Chemistry"), Volume XII/2, to give the esters (I) according to the invention.

The following compounds could be obtained analogously:

Table 12

| Compound No. | Formula | Physical properties (boiling range) |
|---|---|---|
| 1 | ClCH$_2$-CHF-OPO(OCH$_3$)$_2$ | 76–77° C/0.4 mm Hg |
| 2 | BrCH$_2$-CHF-OPO(OCH$_3$)$_2$ | 78° C/0.08 mm Hg |
| 3 | ClCH$_2$-CHF-OPO(OC$_2$H$_5$)$_2$ | 78–80° C/0.1 mm Hg |
| 4 | BrCH$_2$-CHF-OPO(OC$_2$H$_5$)$_2$ | 75–77° C/0.1 mm Hg |
| 5 | (ClCH$_2$-CHF-O-)$_2$PO(OCH$_3$) | 108–112° C/0.15 mm Hg |
| 6 | CH$_3$-PO(OCH$_3$)(OCHF-CH$_2$Cl) | 110° C/11 mm Hg |
| 7 | CH$_3$-PO(OCH$_3$)(OCHF-CH$_2$Br) | 90–93° C/0.1 mm Hg |
| 8 | C$_2$H$_5$PO(OC$_2$H$_5$)(OCHF-CH$_2$Cl) | 58° C/0.2 mm Hg |
| 9 | C$_2$H$_5$-PO(OC$_2$H$_5$)(OCHF-CH$_2$Br) | 80–85° C/0.5 mm Hg |
| 10 | CH$_3$O-PO(OCH$_2$-CH$_2$Cl)(OCHF-CH$_2$Cl) | 108–112° C/0.4 mm Hg |
| 11 | (ClCH$_2$-CHF-O-)$_2$PO(OCH$_2$-CH$_2$Cl) | 146° C/0.4 mm Hg |
| 12 | n-C$_3$H$_7$PO(O-nC$_3$H$_7$)(OCHF-CH$_2$Cl) | 70–72° C/0.2 mm Hg |
| 13 | ClCH$_2$-CF$_2$-O-PO(OCH$_3$)$_2$ | 100–102° C/11 mm Hg |
| 14 | CH$_3$-PO(OCH$_2$-CH$_2$Cl) (OCHF-CH$_2$Cl) | 95–100° C/0.2 mm Hg |

Other compounds which can be similarly prepared include:

| Compound NO. | Formula |
|---|---|
| 15 | C$_2$H$_5$-PO(OCH$_2$-CH$_2$Cl) (OCHF-CH$_2$Cl) |
| 16 | C$_2$H$_5$-PO(OCH$_3$) (OCHF-CH$_2$Cl) |
| 17 | C$_2$H$_5$-PO(OCHCH$_2$Cl-CH$_3$) (OCHF-CH$_2$Cl) |
| 18 | CH$_3$O-PO(OC$_2$H$_5$) (OCHF-CH$_2$Br) |

It will be appreciated that the instant specification and examples are set forth by way of illustration and not limitation, and that various modifications and changes may be made without departing from the spirit and scope of the present invention.

What is claimed is:

1. A 1-fluoro-2-halogeno-ethyl-phosphoric(phosphonic) acid ester of the formula

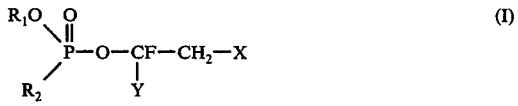

in which
R$_1$ is alkyl with 1 to 4 carbon atoms optionally substituted by fluorine, chlorine or bromine,
R$_2$ is alkyl with 1 to 4 carbon atoms and optionally substituted by fluorine, chlorine or bromine,
X is chlorine or bromine, and
Y is hydrogen or fluorine.

2. A method of combating insects, acarids or nematodes which comprises applying to the insects, acarids or nematodes or to a habitat thereof an insecticidally, acaricidally or nematicidally effective amount of a compound according to claim 1.

3. The method according to claim 2 in which the active compound is

O-methyl-O-[1-fluoro-2-chloroethyl]-methanephosphonic acid ester,

O-methyl-O-[1-fluoro-2-bromoethyl]-methanephosphonic acid ester, or

O-ethyl-O-[1-fluoro-2-chloroethyl]-methanephosphonic acid ester.

4. An insecticidal, acaricidal or nematicidal composition containing as active ingredient an insecticidally, acaricidally or nematicidally effective amount of a compound according to claim 1 in admixture with a diluent.

5. A compound according to claim 1, in which $R_1$ is methyl, ethyl, 2-chloroethyl, 2-bromoethyl, n-propyl, isopropyl, 1-chloro-isopropyl, n-butyl, sec.-butyl, 2-chloro-1-fluoroethyl, or 2-bromo-1-fluoroethyl, and $R_2$ is methyl, ethyl, n-propyl, n-butyl or 2-chloroethyl.

6. The compound according to claim 1, wherein such compound is O-methyl-O-[1-fluoro-2-chloroethyl]-methanephosphonic acid ester of the formula

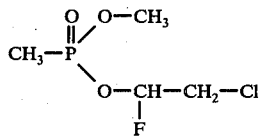

7. The compound according to claim 1, wherein such compound is O-methyl-O-[1-fluoro-2-bromoethyl]-methanephosphonic acid ester of the formula

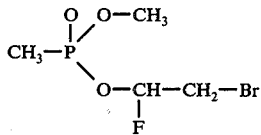

8. The compound according to claim 1, wherein such compound is O-ethyl-O-[1-fluoro-2-chloroethyl]-ethanephosphonic acid ester of the formula

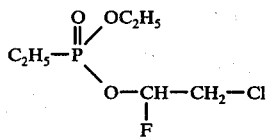

9. A 1-fluoro-2-halogeno-ethyl-phosphoric(phosphonic) acid ester of the formula

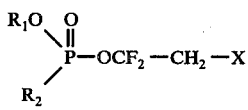

in which $R_1$ is alkyl with 1 to 4 carbon atoms optionally substituted by fluorine, chlorine or bromine, $R_2$ is alkoxy with 1 to 4 carbon atoms and substituted by fluorine, chlorine or bromine, and X is chlorine or bromine.

10. A method of combating insects, acarids or nematodes which comprises applying to the insects, acarids or nematodes or to a habitat thereof an insecticidally, acaricidally or nematicidally effective amount of a compound according to claim 9.

11. An insecticidal, acaricidal or nematicidal composition containing as active ingredient an insecticidally, acaricidally or nematicidally effective amount of a compound according to claim 9 in admixture with a diluent.

12. A compound according to claim 1, in which $R_1$ is methyl, ethyl, 2-chloroethyl, 2-bromoethyl, n-propyl, isopropyl, 1-chloroisopropyl, n-butyl, sec.-butyl, 2-chloro-1-fluoroethyl or 2-bromo-1-fluoroethyl, and $R_2$ is methoxy, ethoxy, 2-chloroethoxy, 2-bromoethoxy, n-propoxy, isopropoxy, 1-chloro-isopropoxy, n-butoxy, sec.-butoxy, 2-chloro-1-fluoroethoxy or 2-bromo-1-fluoroethoxy.

* * * * *